United States Patent [19]
Schmitt

[11] Patent Number: 5,376,557
[45] Date of Patent: Dec. 27, 1994

[54] PROCESS FOR THE DETERMINATION OF ANTIBODIES WHICH ARE CLASS-SPECIFIC FOR AN ANTIGEN AND A REAGENT FOR CARRYING OUT THE PROCESS

[75] Inventor: Urban Schmitt, Oberhausen, Germany

[73] Assignee: Boehringer Mannheim GmbH, Mannheim-Waldhof, Germany

[21] Appl. No.: 923,026

[22] Filed: Jul. 30, 1992

Related U.S. Application Data

[63] Continuation of Ser. No. 723,706, Jun. 24, 1991, abandoned, which is a continuation of Ser. No. 427,036, Oct. 25, 1989, abandoned.

[30] Foreign Application Priority Data

Oct. 25, 1988 [DE] Germany .............................. 3836348

[51] Int. Cl.$^5$ ................. G01N 33/563; G01N 33/566; G01N 33/536; G01N 33/537
[52] U.S. Cl. .................................. 436/513; 436/501; 436/512; 436/536; 436/538; 436/540; 436/541; 435/7.92; 435/7.93; 435/7.94; 435/7.95
[58] Field of Search ............... 436/501, 513, 512, 536, 436/538, 540, 541; 435/7.92, 7.93, 7.94, 7.95

[56] References Cited

U.S. PATENT DOCUMENTS

| | | | |
|---|---|---|---|
| 4,020,151 | 4/1977 | Bolz et al. | 424/1.5 |
| 4,292,403 | 9/1981 | Duermeyer | 435/5 |
| 4,347,311 | 8/1982 | Schmitz | 435/7 |
| 4,376,110 | 3/1983 | David et al. | 436/513 |
| 4,496,654 | 1/1985 | Katz et al. | 435/7 |
| 4,548,909 | 10/1985 | Parratt | 435/7 |
| 4,600,690 | 7/1986 | Karmen et al. | 435/7 |
| 4,931,385 | 6/1990 | Block et al. | 435/7 |

FOREIGN PATENT DOCUMENTS

| | | | |
|---|---|---|---|
| 0005271 | 11/1979 | European Pat. Off. | |
| 0173295 | 6/1985 | European Pat. Off. | 435/7 |
| 2026691 | 2/1980 | United Kingdom . | |
| 2203836 | 10/1988 | United Kingdom . | |

OTHER PUBLICATIONS

Gerlich, et al. Cutoff Levels of Immunoglobulin M Antibody against Viral Core Antigen for Differentiation of Acute, Chronic, and Past Hepatitis B Virus Infections. J. Clin. Micro vol. 24, No. 2, pp. 288–293 (1986).

Hinds, et al., "Ligand Displacement Immunoassay: A Novel Enzyme Immunoassay Demonstrated for Measuring Theophylline in Serum" Clinical Chemistry 30/7, 1174 (1984).

Walls, Enzyme Immunoassays, Ch. 20., Molecular Immunology; Ed. Atassi, et al. (1984).

Ginsberg, H. S. (1980) Hepatitis Virus In: Microbiology. Davis, Dulbecco, Eisen, Ave).

Ginsberg, Eds. Harper and Row, N.Y. pp. 1220–1229.

Jawetz et al. (1987) Hepatitis Virus In: Review of Medical Microbiology. Jawetz et al. Ed. Appleton & Lang, Los Altos pp. 443–456.

White et al. (1986) Hepadna-Viruses, In: Medical Virology, White et al Eds. Academic Press, N.Y. pp. 370–375.

Primary Examiner—David Saunders
Assistant Examiner—D. R. Preston
Attorney, Agent, or Firm—Felfe & Lynch

[57] ABSTRACT

The present invention provides a method for type determination in body fluids of antibodies of a definite immunoglobulin class which are directed against an antigen A according to the immunoassay principle by incubation of the sample solution with at least two receptors $R^1$ and $R^2$, of which $R^1$ is immobilizable and binds with the antibody to be determined and $R^2$ is labelled and binds either with the antibody to be determined or with the antigen A, separation of the solid phase from the liquid phase and measurement of the label in one of the two phases, wherein the immunological reaction is carried out in homogeneous phase and the sample solution is incubated simultaneously with receptor $R^1$ and an excess of human antibodies or fragments thereof which belong to the same immunoglobulin class as the antibody to be determined and are not bindable with the antigen A and subsequently receptor $R^2$ and possibly further receptors are added thereto. The present invention also provides a reagent for carrying out this method.

13 Claims, No Drawings

PROCESS FOR THE DETERMINATION OF ANTIBODIES WHICH ARE CLASS-SPECIFIC FOR AN ANTIGEN AND A REAGENT FOR CARRYING OUT THE PROCESS

This application is a continuation, of application Ser. No.07/723,706, filed Jun. 24, 1991, now abandoned, which is a continuation of application Ser. No. 07/427,036, filed Oct. 25, 1989, now abandoned.

The present invention is concerned with a method for the determination in body fluids of class-specific antibodies which bind to an antigen by incubating a body fluid sample with at least two receptors $R^1$ and $R^2$, of which $R^1$ can be immobilized and binds with the class specific antibody to be determined and $R^2$ is labelled and specifically binds with either of the class specific antibody to be determined or with the antigen for which the antibody to be determined is specific, immobilizing $R^1$ on a solid phase, separating the solid phase from the liquid phase and measuring the label in one of the two phases as a measure of the class specific antibody. The present invention is also concerned with a reagent for carrying out this method.

In response to the introduction of foreign substances, the mammalian body produces antibodies, also referred to as immunoglobulins. Immunoglobulins can be divided up into 5 classes which differ in their construction and function. The different immunoglobulin classes perform different tasks in the organism. For example following the first introduction, or immunization with a foreign substance, immunoglobulin of class M ("IgM") is formed. The concentration of IgM, however, rapidly decreases in progressive infection. Immunoglobulin of class G (i.e., "IgG"), initially formed slowly after first immunization, but are produced in large amounts following a second encounter with the same foreign substance. Immunoglobulins of class A ("IgA") are responsible for defense processes on the mucous membrane surfaces of the organism. Immunoglobulins of class E ("IgE") are mainly responsible for allergic reactions. Relatively little is known about immunoglobulin of class D ("IgD").

The individual immunoglobulin classes occur in the blood in greatly differing concentrations. Thus, the IgG content in the serum of normal persons is in the range of from 8 to 16 mg/ml. Antibodies of the IgM class are present in the serum in an amount of from 0.5 to 2 mg/ml. The second most frequently occurring immunoglobulin is IgA which is present in the serum of normal persons in the range of from 1.4 to 4 mg/ml. The smallest is the concentration of IgE in the serum which is present in the range from 0.000017 to 0.00045 mg/ml. The content of IgD in the serum is in the range of from 0 to 0.4 mg/ml.

For diagnosis, it is of interest to detect antibodies of a particular immunoglobulin class which are specific for a particular antigen. In this way, differential diagnosis can be made in for, e.g., viral, bacterial and parasitic infections. IgG and IgM determination is especially suitable for differentiation between fresh and long-standing infections, as well as for monitoring the course of an infection. In particular, determination of class-specific antibodies is useful in diagnosing hepatitis B, toxo-plasmosis, rubella and Chlamydia infections.

Processes are known for the determination of class-specific antibodies. Thus, for example, in U.S. Pat. No. 4,020,151, a process is described for the determination of IgG, IgA and IgM concentrations in the serum. The described processes teaches that a solid carrier is first reacted with the sample solution, IgG, IgA or IgM thereby being adsorbed on the solid phase. Subsequently labelled antibodies against the particular Ig class are added thereto and the bound labelling is evaluated. Another detection system is described by W. Duermeyer et al., The Lancet II, 684-685, in which an antibody for a specific class of immunoglobulin is bound to a solid carrier. After addition of the sample, the class-specific immunoglobulins are bound to the wall and, in a second step, the antigen specific for the antibody to be determined is added, which then binds to the antibody. In a third step, a labelled antibody directed against this antigen is added thereto and again the proportion of the bound labelling is determined.

These previously known processes for the determination of class-specific immunoglobulins are, however, not satisfactory. Because of the limited binding capacity of the solid phase and the high analyte concentration in the sample, only a small proportion of the immunoglobulin classes contained in the serum can be bound. Therefore, this results in great variations in quantitative determination of the antigen-specific immunoglobulins since the totality of these immunoglobulins in the serum are subject to great variations. In samples where the variations among antibodies in a given class is very high, known processes are not useful at all. Different measurements are obtained and, in extreme cases, a positive sample may be evaluated as being negative.

In order to reduce these disturbances, it has been suggested, in Journal of Clinical Microbiology, August, 1986, pages 288-293, to dilute the sample solution, then to add serum which contains antibodies of the immunoglobulin class to be determined and then to dilute the sample further. In the case of this process, dilutions of 1:20000 are necessary. On the one hand, due to this high dilution, the reproducibility of the results obtained is questionable and, on the other hand, this process cannot be transferred to automatic analyzers.

Therefore, it is an object of the present invention to provide a process by which class-specific antibodies for an antigen can be determined quantitatively in body fluid samples without a laborious sample preparation or high dilution of the sample being necessary, which process can be carried out in a few steps.

Thus according to the present invention, there is provided a process for the determination in body fluids of antibodies of a particular immunoglobulin class which are directed against an antigen A. The invention is carried out by incubating the sample solution with at least two receptors $R^1$ and $R^2$ of which $R^1$ is immobilisable to a solid phase and binds with the antibody to be determined, and $R^2$ is labelled and binds either with the antibody to be determined or with the antigen A, separating the solid phase from the liquid phase and measurement of the labelling in one of the two phases, wherein the immunological reaction is carried out in homogeneous phase and the sample solution is simultaneously incubated with receptor $R^1$ and an excess of human antibodies or fragments thereof which belong to the same class of immunoglobulins as the antibody to be determined which do not bind with the antigen A. Subsequently, receptor $R^2$ and possible further receptors are added thereto.

Surprisingly, with the process according to the present invention, it is possible reproducibly to detect class-specific antibodies without pretreatment of the sample having to take place. The process according to the present invention can be carried out simply and quickly.

According to the present invention, the antibodies class-specific for an antigen A are determined in a homogeneous immunoassay, i.e. the immunological reaction takes place in homogeneous phase. For this purpose, as receptor $R^1$ which is bindable with the antibody to be determined, an immobilizable receptor is used which, during the immunological reaction, is present in homogeneous phase and is immobilized on a solid phase. Therefore, receptor $R^1$ contains a part which renders it bindable to the solid phase and a part which binds with the class-specific antibody. Preferably, this later portion is an antibody or a binding fragment or derivative thereof directed against a constant part of the class specific antibody. Thus, if immunoglobulin of class G is to be determined, then the receptor $R^1$ contains anti-IgG antibody or a Fab fragment thereof. For immobilization, a receptor bindable with the constant part of receptor $R^1$ can be immobilized on the solid phase. Preferably, however, as $R^1$ is a conjugate of a first portion which binds with the class-specific antibody and a partner of a specifically bindable pair. Especially preferred in this regard is biotin. As solid phase, a matrix to which the other partner of the specifically-binding pair, such as streptavidin is bound is preferred. The immobilization then takes place by binding of the two partners with one another. Since this binding takes place heterogeneously and thus very much more slowly than the immunological reaction, this does not impair the carrying out of the immunological reaction in homogeneous phase.

In another variant of this process, the solid phase has bound thereto the same partner of the specifically binding pair, such as biotin. In carrying out the immobilization, the other partner of the specifically binding pair is added thereto. This brings about binding between the solid phase and receptor $R^1$.

In order to carry out the process according to the present invention an excess of human class-specific antibody or the immunoglobulin class to be determined or fragments thereof which, however, do not bind with the antigen A are added and reacted with $R^1$, e.g., by incubation with $R^1$, is added to the sample solution and receptor $R^1$. As fragments, there can thereby be used the Fc fragments of the immunoglobulin class to be determined or the H-chain antigen determinants. Thus, for the detection of IgM, there can be used the $\mu$-chain, for the detection of IgG the $\gamma$-chain etc.

Preferably, the human class-specific antibody is added in an excess of 2 to 100:1, referred to the amount of immunoglobulin to be expected in the sample solution.

Preferably a solution of receptor $R^1$ and the excess of the class-specific antibody is formed first. The part of the receptor $R^1$ bindable with the antibody to be determined thereby reacts with the added class-specific antibodies. Subsequently, the sample solution is added thereto. The class-specific antibodies of the sample which are now present in insufficiency in the sample solution partly displace non-specific antibodies present in excess from complexes formed with receptor $R^1$ The displacement depends on the affinity of the class-specific antibodies for $R^1$. It occurs more rapidly if the affinity is low. Preferably class-specific antibodies with an affinity of $<5\times10^{-9}$ 1/mole for $R^1$ were used. Receptor $R^2$ is then added, and this binds to the complex of antibody to be determined and receptor $R^1$. After immobilization, the proportion of bound label can then be determined in known manner, this being a direct measure for the amount of class-specific antibody in the sample solution.

The amount of added class-specific antibody is not critical but it should be at least twice as great as the upper limiting value which can normally be expected for immunoglobulins of this class in the serum. Therefore, the excess preferably amounts to 2:1 to 100:1, referred to the expected amount of immunoglobulin. In the case of an excess of more than 100 fold, no further improvement is obtained so that a still greater excess is uneconomic.

As second receptor, a labelled receptor is used. Labelling takes place in known manner and can be a radioactive isotope, a chemiluminescent or fluorescing substance, a substance forming a colored material or an enzyme. Processes for the detection of these labellings are known and do not, therefore, need to be explained. Receptor $R^2$ is bindable either with the antibody to be determined or with the antigen specific for this antibody. In the first variant as receptor $R^2$, the antigen specific for the antibody to be determined is used. This is labelled in known manner. In the other variant, as receptor $R^2$, an antibody or fragment thereof directed against the antigen specific for the antibody to be determined is preferred. The antibody can be monoclonal or polyclonal. In this second embodiment a further receptor $R^3$ is necessary which is a substance specifically bindable with the antibody to be determined and with $R^2$. $R^3$ contains preferably the antigen specific for the antibody to be determined. The antigen can be used as $R^3$ if said antigen has binding sites (epitopes) for the antibody to be determined and for $R^2$.

In order to carry out the process according to the present invention, the sample solution is first incubated with receptor $R^1$ and the excess of the class-specific antibody. Subsequently receptor $R^2$ is added thereto. In the variant in which receptor $R^3$ is used, this is added to the sample solution before the addition of receptor $R^2$.

Especially preferred is the form of carrying out the process according to the present invention in which only two receptors are necessary so that the reaction can be carried out in two steps and thus a transfer to an automatic analyzer is possible.

The immunological reaction takes place in homogeneous phase, which is very advantageous since the homogeneous reaction proceeds quicker and more reproducibly than the heterogenoeus reaction.

The present invention also provides a reagent for the determination of antibodies in body fluids which are class-specific for an antigen A, which reagent contains a first solution which is a mixture of receptor $R^1$ which is immobilisable and binds with the antibody to be determined and an excess of human class-specific antibodies which cannot bind with the antigen A and a second solution containing receptor $R^2$ which is labelled and contains antigen A.

In a further variant, the reagent according to the present invention has, a first solution, a mixture of receptor $R^1$ and an excess of human class-specific antibodies which do not bind with antigen A, as second solution, receptor $R^2$ which is labelled and contains an antibody directed against antigen A, and a third solution containing receptor $R^3$ which comprises antigen A.

In this variant, receptor $R^3$ must have at least one binding site for the specifically-bindable antibody and at least one binding site for receptor $R^2$. Therefore receptor $R^3$ is an antigen which is polyvalent. If, however an antibody against an antigen which is monovalent is to be detected, $R^3$ is the antigen in polymeric form. For this purpose, the antigen can be bound to a carrier, for example bovine serum albumin, latex or a microcarrier, or can be cross-linked. Processes for this purpose are well known.

In a preferred embodiment, the second solution and third solution of the reagent can be premixed. The reagent then contains, as first solution, a mixture of receptor $R^1$ and an excess of human class-specific antibodies which do not bind to antigen A and, as second solution, receptor $R^2$ which is labelled and contains an antibody directed against antigen A and receptor $R^3$ which comprises the antigen A.

The reagent contains the human class-specific antibody in such an excess that, referred to the amount of immunoglobulin to be expected in the sample solution, a 2 to 100 fold amount of human class-specific antibody is present in the reaction solution. For this purpose, for the case in which 10 μl of sample are to be added to 1 ml of reagent, the reagent preferably contains about 20 to 2000 mg of antibody per liter.

The reagent according to the present invention contains, in two or three separate solutions, the components necessary for the determination of class-specific antibodies. The solutions are stored physically separated from one another and, for the determination, are successively incubated with the sample solution. The solutions are storage stable.

The following Examples are given for the purpose of illustrating the present invention:

EXAMPLE 1

Anti-HBcAG antibody of immunoglobulin class M was determined in serum. For this purpose, as solid phase a test tube coated with streptavidin was used. 10 μl of sample were added, together with 1000 μl of a reagent of the following composition:

Reagent 1:
40 mMole/liter phosphate buffer (pH
0.5% Pluronic F68, 0.2% bovine serum albumin,
0.01% phenol, 40 mg/liter human IgM which is not bindable with HBcAG and 2 mg/liter of a monoclonal antibody against IgM which has been coupled with biotin.

Incubation took place at ambient temperature for 30 minutes. After washing three times with water, 1 ml of a reagent of the following composition was added thereto:

Reagent 2:
40 mMol/liter phosphate buffer (pH 7.0),
0.2% bovine serum albumin, 0.01% phenol,
75 μg/liter hepatitis core antigen and
25 U/liter of a conjugate of a monoclonal anti-HBcAG antibody and peroxidase.

A period of incubation of 60 minutes at 20° to 22° C. and washing three times with water, followed by addition of 1 ml of ABTS solution as substrate were the relevant protocols. Extinction was determined after 1 hour at 405 nm and evaluation on the basis of a calibration curve. The results obtained are given in the following table:

| serum No. | without addition of human IgM in the reagent | | with addition of human IgM in the reagent | |
|---|---|---|---|---|
| | absorbance (mE) | % deval. from the average[1] | absorbance (mE) | % deval. from the average[2] |
| 1 | 235 | 132 | 465 | 103 |
| 2 | 119 | 67 | 397 | 88 |
| 3 | 216 | 121 | 471 | 104 |
| 4 | 120 | 67.4 | 437 | 97 |
| 5 | 211 | 119 | 493 | 109 |
| 6 | 92 | 52 | 385 | 85 |
| 7 | 161 | 90 | 460 | 102 |
| 8 | 276 | 155 | 496 | 110 |
| 9 | 194 | 109 | 461 | 102 |
| 10 | 159 | 89 | 444 | 98 |

[1]average: 179
[2]average: 451

EXAMPLE 2

Anti-HBc antibody of the IgM class was determined in serum analogously to Example 1 but, instead of the biotinylated monoclonal antibody against human IgM, there a biotinylated polyclonal anti-human IgM antibody was used as Reagent 1. The evaluation took place in the manner described in Example 1.

EXAMPLE 3

Anti-HBcAG antibodies of class IgM in serum were detected, using the protocol described in Example 1. A conjugate of HBcAG and peroxidase was used, however instead of the antibody POD conjugate and the hepatitis core antigen in Reagent 2. The evaluation took place in the manner described in Example 1.

It will be understood that the specification and examples are illustrative but not limitative of the present invention and that other embodiments within the spirit and scope of the invention will suggest themselves to those skilled in the art.

I claim:

1. Method for determining an IgM class of immunoglobulin which specifically binds to an antigen A in a body fluid sample comprising:
    (i) first contacting said body fluid sample containing antigen A with a mixture of a receptor $R^1$ which specifically binds with said immunoglobulin class to be determined and which contains human anti-IgM antibodies or Fab fragments thereof, and human antibodies or human antibody fragments which are members of the IgM class of immunoglobulin to be determined but do not bind to antigen A, said human antibodies being present in an excess relative to a range of said IgM immunoglobulin class to be determined, and under conditions effective to form a complex between $R^1$ and said IgM class of immunoglobulin to be determined;
    (ii) next contacting said body fluid sample with a labelled receptor $R^2$ which binds with said IgM class of immunoglobulin to be determined under conditions favoring binding to its reaction partner;
    (iii) contacting said body fluid sample with a solid phase which immobilizes $R^1$;
    (iv) separating said solid phase and liquid phase, and,
    (v) measuring label in one of said solid and liquid phase as a measurement of said IgM class of immunoglobulin to be determined.

2. Method of claim 1, wherein $R^1$ comprises a conjugate of biotin and an antibody or bindable fragment thereof.

3. Method of claim 2, wherein $R^1$ is immobilized to a solid phase containing avidin or streptavidin.

4. Method of claim 1, wherein said human antibodies or fragments are fragments selected from the group consisting of Fc and heavy chain fragments.

5. Method of claim 1, wherein said human antibodies or fragments thereof are present in an excess ranging from about 2:1 to about 100:1 relative to expected concentration of IgM class immunoglobulin to be determined.

6. Method for determining an IgM class of immunoglobulin which specifically binds to an antigen A in a body fluid sample comprising:
   (i) first contacting said body fluid sample containing antigen A with a mixture of a receptor $R^1$ which specifically binds with said IgM immunoglobulin class to be determined and which contains human anti-IgM antibodies of Fab fragments thereof, and human antibodies or human antibody fragments which are members of the class of the IgM class of immunoglobulin to be determined but do not bind to antigen A, said human antibodies being present in an excess relative to a range of said IgM immunoglobulin class to be determined under conditions effective to form a complex between $R^1$ and said IgM class of immunoglobulin to be determined;
   (ii) next contacting said body fluid sample with a labelled receptor $R^2$ which binds with said antigen A under conditions favoring binding to its reaction partner;
   (iii) contacting said body fluid sample with a third receptor $R^3$ comprising antigen A;
   (iv) contacting said body fluid sample with a solid phase which immobilizes $R^1$;
   (v) separating said solid phase and liquid phase, and,
   (vi) measuring label in one of said solid and liquid phase as measurement of said IgM class of immunoglobulin to be determined.

7. Method of claim 6, wherein $R^1$ comprises a conjugate of biotin and an antibody or bindable fragment thereof.

8. Method of claim 6, wherein $R^1$ is immobilized to a solid phase containing avidin or streptavidin.

9. Method of claim 6, wherein said human antibodies or fragments are fragments selected from the group consisting of Fc and heavy chain fragments.

10. Method of claim 6, wherein said human antibodies or fragments thereof are present in an excess ranging from about 2:1 to about 100:1 relative to expected IgM class of immunoglobulin concentration to be determined.

11. Reagent useful in determining an IgM class of immunoglobulin which specifically binds to an antigen A comprising a first solution containing a mixture of receptor $R^1$ which specifically binds to said IgM class immunoglobulin to be determined and which contains anti-IgM antibodies or Fab fragments thereof, and human antibodies or human antibody fragments of the same class as the IgM class of immunoglobulin to be determined which human antibodies do not bind to said antigen A and which are present in an excess relative to expected concentration of said IgM class immunoglobulin to be determined, and a separate second solution containing receptor $R^2$ which is labelled and contains antigen A.

12. Reagent useful in determining an IgM class immunoglobulin which specifically binds to an antigen A comprising a first solution containing a mixture of receptor $R^1$ which specifically binds to said IgM class immunoglobulin to be determined and which contains anti-Igm antibodies or Fab fragments thereof, and human antibodies or fragments thereof of the same class as the class of IgM immunoglobulin to be determined, which human antibodies or fragments do not bind to said antigen A, said human antibodies or fragments being present in an excess relative to the expected concentration of said IgM class immunoglobulin to be determined, a separate second solution containing receptor $R^2$ which is labelled and contains an antibody which specifically binds to said antigen A, and a separate third solution containing receptor $R^3$ which contains antigen A.

13. Reagent useful in determining an IgM class immunoglobulin which specifically binds to an antigen A comprising a first solution containing a mixture of receptor $R^1$ which specifically binds to said IgM class of immunoglobulin to be determined and which contains anti-IgM antibodies or Fab fragments thereof, and human antibodies or fragments thereof of the same class as the IgM class of immunoglobulin to be determined which human antibodies or fragments thereof do not bind to said antigen A, said human antibodies or fragments being present in an excess relative to expected concentration of said IgM class of immunoglobulin to be determined, and a separate second solution containing receptor $R^2$ which is labelled and contains an antibody which specifically binds to said antigen A, said second solution containing receptor $R^3$ which contains antigen A.

* * * * *